(12) United States Patent
Rushbrooke

(10) Patent No.: US 7,170,597 B1
(45) Date of Patent: Jan. 30, 2007

(54) MICROPLATE READER

(75) Inventor: John Gordon Rushbrooke, deceased, late of Newport Beach, CA (US); by Claire Elizabeth Hooper, legal representative, Newport Beach, CA (US)

(73) Assignee: Packard Instrument Company, Inc., Meriden, CT (US)

( * ) Notice: Subject to any disclaimer, the term of this patent is extended or adjusted under 35 U.S.C. 154(b) by 0 days.

(21) Appl. No.: 10/018,387

(22) PCT Filed: Apr. 20, 2000

(86) PCT No.: PCT/GB00/01576

§ 371 (c)(1),
(2), (4) Date: Jun. 5, 2002

(87) PCT Pub. No.: WO01/01112

PCT Pub. Date: Jan. 4, 2001

(30) Foreign Application Priority Data

Jun. 26, 1999 (GB) .................................. 9914902.3
Jun. 29, 1999 (GB) .................................. 9915032.8

(51) Int. Cl.
*G01J 3/30* (2006.01)

(52) U.S. Cl. ................... 356/317; 356/318; 250/458.1; 250/459.1

(58) Field of Classification Search ............... 356/417, 356/422, 317, 318; 250/459.1, 458.1
See application file for complete search history.

(56) References Cited

U.S. PATENT DOCUMENTS

| | | | | |
|---|---|---|---|---|
| RE34,782 E | * | 11/1994 | Dandliker et al. | ........ 250/458.1 |
| 5,891,738 A | * | 4/1999 | Soini et al. | .................. 436/501 |
| 5,949,532 A | * | 9/1999 | Schrof et al. | .................. 356/73 |
| 6,686,582 B1 | * | 2/2004 | Volcker et al. | ............. 250/216 |

FOREIGN PATENT DOCUMENTS

| | | |
|---|---|---|
| DE | 197 48 211 | 5/1999 |
| GB | 2 315 131 | 1/1998 |
| WO | WO 97/34171 | 9/1997 |
| WO | WO 98/30889 | 7/1998 |

* cited by examiner

*Primary Examiner*—Layla G. Lauchman
(74) *Attorney, Agent, or Firm*—Barnes & Thornburg LLP

(57) ABSTRACT

A method and apparatus for the measurement of radiation, especially fluorescence from samples in assays, wherein a plurality of micro-sample light emitting sites are imaged simultaneously onto a detector array by a plurality of miniature objectives, one for each sample site and focussed thereon, producing parallel beams of light arranged in parallel and spaced apart, which beams are focussed at a pinhole aperture and then reconstituted as parallel beams for incidence on the detector array.

44 Claims, 6 Drawing Sheets

Example of microcapillary channels in an 8 x 12 pattern, similar to the wells in a 96-well microtitre plate High density miniaturised well format presentation having 3456 wells Enlarged view of part of a high density gridded array of, eg, DNA

MICROPLATE READER

FIELD OF INVENTION

This invention relates to the measurement of radiation, typically but not essentially fluorescence emitted by samples and assays in the field of biological, bio-medical and chemical sciences.

BACKGROUND TO THE INVENTION

Such assays are normally prepared and measured in sample plates or formats, including 96-well microtitre plates, petri dishes, gel matrices, membranes, glass slides and capillaries. The trend is towards higher throughput detection of samples and the use of smaller volumes in each of the samples, resulting in so-called miniaturised sample formats.

This requires the corresponding development of detectors capable of handling such miniaturised formats. This is particularly so in the case of high throughput screening (HTS) of biological assays as applied to drug discovery and the screening of drug candidates.

Such miniaturisation is achieved by arranging samples for assay and detection in well plates in which typically there can be 96, 384, 864, 1536 or 3456 wells per plate, and sample volumes can vary from 200 microlitres to as little as 1 microlitre.

Alternative formats for the miniaturisation of assays include capillaries, microchannels or microfluidic structures, including microwells, which can be moulded or etched in substrates such as glass (eg silica or quartz) or plastic. In these alternative formats, the sample volumes can be of the order of nanolitres and picolitres.

In order to achieve high throughput screening it is necessary to interrogate large numbers of such samples simultaneously. In the case of fluorescence based assays, detection or interrogation consists of illuminating each sample with excitation light, and subsequently detecting the emitted fluorescence from each sample separately. Examples of fluorescent based processes include prompt fluorescence and time-resolved fluorescence where there is a time delay between photoactivation of the sample and emission, in the range, for example of ps to ms or more. A further process is fluorescence or luminescence energy transfer. In this process a molecule is activated, for example by excitation light, and transfers energy via eg resonance energy transfer or chemical transfer to a second molecule, which in turn emits light. This process can involve different or multiple secondary molecules, which can emit radiation over a range of wavelengths. Further examples of luminescent processes include phosphorescence, and chemi- and bio-luminescence. Wavelength ranges for all these processes include UV, visible, red and infra-red (approx 250–1200 nm).

In a typical arrangement, a scanning head with 96-channels simultaneously interrogates the 96-sites arranged in the 8×12 pattern of a 96-well microtitre plate. By stepping a larger well density plate relative to the 96-channel scanning head, the remaining sites can be read eg 2×2 steps will cover 384-samples, 6×6 steps will cover 3456 samples, and so on, so as to address a high density sample presentation format.

Fluid samples, eg liquids or gels, can be placed in small sample sites, such as micro-capillaries or microchannels, which can be typically 100×100 um in section, and typically 1–100 mm long. The samples can be moved by pumps, or electrophoretically or electro-osmotically. Samples can be solid or a matrix, such as beads, agarose or microparticles, suspended or otherwise contained in a fluid medium, including a gel type format. Other samples can comprises suspensions or monolayers of cells.

Applications include cell biology, hybridisation techniques and immunoassays including binding assays. In such assays, materials can be labelled with a fluorescence marker for the purpose of identification. In a binding assay, a bound molecule can be separated from an unbound molecule, as between a solid and liquid medium. Further applications include electrophoresis or electro-osmosis fluids such as liquids in gels and media including agarose. Such applications can be run in miniaturised formats including microcapillaries and micro-fluidic structures, where molecules of moities may be separated spatially by properties including molecular weight or charge and may also be labelled with fluorescent or luminescent tags or dyes for the purpose of detection and identification. The techniques described herein can be applied to the detection of biological compounds including proteins and nucleic acids, and in cell biology, processes such as cell signalling or cell binding can also be detected.

Separated molecules can be contained in a fixed matrix, such as a gel or agarose beads, or can be separated in a fluid such that the separated molecules or moities will flow at different rates through a medium and can be detected at a fixed point along the flow path as a series of emission peaks based on their time separation profile. It is important that emission detection methods posses high accuracy and sensitivity for the determination of such peaks, and the rapid and/or continuous and/or simultaneous measurement of samples.

A number of such assay techniques involve time changes in light emission. To measure such changes requires an ability to perform rapid, accurate, sensitive and repetitive readings, that is to perform kinetic measurements. In order to achieve high throughput it is necessary for a system to measure multiple samples simultaneously, requiring high resolution, high sensitivity and high signal detection efficiency.

Mostly the samples/assays are arranged to emit light in the middle range, although the quantities of light per sample can be very low.

A further issue with fluorescence-based assays is the problem of quench which causes a reduction in light emission. This can occur in samples and assays particularly those involving cells, due to chemical effects which interfere with the light signal, or due to coloured substances or particles in the sample or medium, which reduce the light signal. In certain applications, such as inhibition assays, a change or reduction in light signal is the feature of the assay requiring measurement.

FIG. 1(a) of the accompanying drawings shows an array of 8×12 micro capillaries in a substrate, in which either a liquid, or molecules or moities in a fluid, move in the X-direction. This is an example of an array of miniaturised samples such as will be referred to in this application.

FIGS. 1(b) and 1(c) of the accompanying drawings show further examples of arrays that involve high density or miniaturised sample formats.

A confocal microscope is a means for achieving excellent imaging capability whilst possessing a unique depth-discriminating property. (A typical Zeiss system is shown in FIG. 15.5 in "Quantitative fluorescence microscopy", F. W. D. Rost, CUP 1991). A parallel light beam from a laser or other suitable light source can be used for fluorescence excitation. The beam is focused by a microscope objective, down to a spot of typically micron or submicron size, within the sample. The fluorescent light emanating from the spot is focused by the same objective, via a beam splitter, onto a pinhole aperture (a spatial filter), and thence onto the detector. The detector does not accept all the light from out-of-focus planes and so these are imaged less strongly by the spatial filter. Thus detected background fluorescence from the substrate or material surrounding the sample, which is also unavoidingly illuminated, is sharply reduced relative to the wanted signal. Moving the microscope relative to the plurality of sample spots or vice versa, allows the spots to be inspected in sequence or scanned.

A confocal microscope therefore has the essential attributes for interrogating the tiny samples described above, such as micro capillaries.

Firstly, there is excellent spatial resolution to excite a small region of a sample and avoid exciting laterally surrounding material.

Secondly, it has good depth discrimination, which minimises the effects of illumination of the substrate, above and below the sample. Hence the effect of background fluorescence at the detector can be reduced/minimised.

Single channel scanners for the purpose have been reported in the literature. For example, we refer to "DNA sequencing using Capillary array Electrophoresis" by X C Huang, M A Quesada and R A Mathies, Anal. Chem. 1992, 64, 2149–2154. In their apparatus a 32×. NA 0.4, Carl Zeiss microscope objective brings the parallel beam from a 1 mW argon ion laser to a 10 micron diameter spot, within a 100 micron id sample capillary. The fluorescence is collected by the same objective, passed via a beam splitter and, after wavelength selection via spectral filters, is focused onto a 400 micron diameter pinhole. The spatially filtered light is then detected by a photomultiplier. In this apparatus a set of capillaries mounted side by side is interrogated successively by the confocal microscope, by means of relative XY movement between the samples and the microscope. However a serious disadvantage of this approach is that no sample is read continuously but is read at best, on a periodic basis. Typically any one sample can be read about once per second.

Thus a single channel confocal scanner has been used to measure a number of sample sites but only sequentially and not simultaneously, and such a system is not appropriate for high throughput scanning where simultaneous detection and assessment of a large number of sites is required, such as in a 96 well microtitre plate or higher density format array or array of microcapillaries.

However, there is known from German Specification No DE 19748211A a system in which a plurality (N) of single channel confocal optical systems and photoelectric detectors or detecting areas are arranged in parallel to form a plurality of reading heads arranged side-by-side so as simultaneously to read a corresponding plurality of adjacent sites. In this known system, the optics include a mask and three focussing lenses which effectively handle the beams emanating from the individual reading heads independently, so that the optical axes of the individual beams are separated.

SUMMARY OF THE INVENTION

According to one aspect of the present invention, there is provided a method of imaging a plurality of micro-sample light emitting sites simultaneously onto separate addressable detectors, which may be discrete regions of the array detector, so that light emitted from each site can be monitored by one of the detectors, wherein a corresponding plurality of objective lenses each comprising a micro-lens are located adjacent to the micro-sample array with one objective lens for each micro-sample, the latter are located at or near the focal point of each of the micro-lenses so that light emanating from each micro-sample is collected by its respective objective lens and converted into a beam of parallel or near parallel rays, the objective lenses are arranged so that the axes of all the beams issuing therefrom are parallel and spaced apart, and the beams are focused by a focussing lens through single point and collected beyond that point by detector lens means which serves to reconstitute the parallel beams for presentation to the detector array, wherein optical discrimination between fluorescence emanating from upstream and downstream regions of the micro-samples is improved by a pinhole aperture located at the focal point of the focussing lens so that light which is not emanating from the focal point of each of the objective lenses adjacent the micro-sample sites will be out of focus at the small aperture pinhole.

The sites may be in a column or in an array such as a microtitre plate.

The optical systems may be arranged in a single line for reading column by column of a multi-column array, or in a staggered pattern for simultaneously viewing sites in different columns if this were preferred.

This system would again comprise essentially (N) independent confocal systems, each with its optic axis aligned with one sample site.

Advantageously only one laser source is provided which may be split into an appropriate plurality of beams, conveyed each by a fibre optic cable to individual sample sites.

The light emitted from the separate sites may in part be conveyed to individual detectors, or discrete regions of an array detector, via optical fibres.

Preferably the reading heads are independently adjustable so each can be positioned accurately over or under a sample. To this end a special opto-mechanical device may be provided to bring each scanner's optic axis into alignment by means of an appropriate scan in the Y-direction.

Where there is a tolerance in the position of the samples, such as in the case of capillaries, which result in uncertainty in the Y-direction, adjustment is preferably provided.

Such an arrangement could be used to inspect say 8 or 12 sites at a time, but an arrangement to inspect larger numbers simultaneously could be costly, complex, and cumbersome. We would refer to such arrangements as "ganged" systems.

The axes of the objectives may be angled if desired with appropriate adjustment of the optical characteristics of the objectives and/or downstream optical system being adapted accordingly.

Preferably and advantageously a single focusing lens (which may be a multi-component lens) is employed for directing all the beam paths through the single point.

The apparatus can be thought of as a single channel imaging system having a plurality of separate paths therethrough the separation of light between one path and another being controlled by careful choice of the quality of the optical components forming the various lens assemblies.

In general the light emitted from the micro-samples will comprise fluorescence of components of the sample. Where the fluorescence is initiated by excitation illumination, fluorescence may be triggered not only from the specific component of the sample which is to be monitored, but also from material around and upstream and downstream of the region of interest. Optical discrimination between fluorescence emanating from upstream and downstream regions can be improved by placing a small aperture pinhole at the focal point of the focusing lens means so that light which is not emanating from the focal point of each of the objective lenses adjacent the micro-sample sites will be out of focus at the small aperture pinhole.

If the aperture size is appropriately selected, out of focus light will be significantly attenuated. On the other hand light emanating from a point in a micro-sample at the focal point of its micro-sample objective lens, will pass through the pinhole relatively unattenuated.

By enlarging the pinhole aperture, more (possibly unwanted) background originating light may pass therethrough but this may be acceptable if in so doing more light can be focused onto the detector from a larger volume within the sample.

According to a preferred feature of this aspect of the invention, the micro-samples are positioned relative to the micro-sample objective lenses so that the region of interest is as close as possible to the focal point of the respective objective lens.

For simplicity, the samples are located on a planar support with the regions of interest all in the same plane so that the objective lenses can likewise all be in the same plane parallel to that containing the regions of interest in the samples.

The method may include the step of adjusting the position of the micro-sample array relative to the lens array and also include the step of individually adjusting the position of at least the objective lenses relative to the micro-samples or vice versa to ensure that the regions of interest in the micro-samples are at the focal point of the respective micro-sample objective lenses.

Where spectral separation is required based on wavelength, a suitable filter can be included in the light path either between the micro-sample objective lenses and the focusing lens means ahead of the pinhole, or between the detector lens and the detector array.

Preferably any such filter is located in a region in which the light paths are parallel or nearly parallel.

Where fluorescence is the mechanism which generates the light which is to be focused onto a detector, excitation radiation to produce the fluorescence is advantageously applied only to the region of interest within each micro-sample rather than over the whole of the micro-sample. To this end the optical elements which determine the path to be traversed by light emanating from the region of interest in each micro-sample, can be used to advantage to inject the excitation radiation onto the micro-sample region of interest, since by doing so, the excitation radiation can be focused onto the region of interest rather than broadly illuminating more or less the whole of the micro-sample.

To this end according to a further preferred feature of the invention, excitation radiation is injected into the multipath optical system so as to proceed in a parallel sense towards the array of objective lenses, in an opposite sense to the light which emanates from the micro-samples, so as to be focused by the objective lenses onto the region of interest in each micro-sample.

Typically the excitation radiation is injected as a parallel beam into the optical path, at right angles thereto, and a 45° beam splitting device is provided onto which the parallel excitation radiation impinges and from which it is directed in a parallel manner towards the micro-sample imaging lenses, but through which light from the micro-samples can pass to the focusing lens.

Typically excitation radiation is produced using a laser such as an argon ion laser, and a beam expander is employed to expand the cross-section of the laser beam into a relatively large area beam equivalent to the area of the parallel array of micro-sample objective lenses.

Where optical light is employed, the beam splitter may be a dichroic mirror.

Whilst in theory the invention can be employed for any number of micro-sample objective lenses, it is advantageous to arrange an 8×12 array of micro-sample objective lenses on the same 8×12 matrix as a standard 96 well plate, and if the imaging system is to be used to inspect for example a 384 well plate, the latter is mounted on an XY stage so that it can be moved relative to the array of objective lenses in manner known per se so as to present groups of 96 wells making up the 384 wells, to the 96 lens array. Thus a 2×2 movement of the XY stage would be required to complete the inspection of all of the well sites in the 384 well array.

According to another optional feature of the invention, the parallel beams of light directed towards the detector array may in part be transferred to the latter via optical fibres, preferably in the form of a fibre optic bundle or fibre optic plate.

According to a further preferred feature of the invention, where a bundle of fibres is employed, the arrangement of the fibres in the bundle may differ between the input and output ends thereof so that the array of fibres which convey the light paths to the different regions of the detector array conforms more to the shape of the detector array in the XY plane and enables for example, optimal utilisation of a generally square array by the rectangular proportions of an 8×12 micro-sample array.

The detector array may typically be a charge coupled device having a large number of separately addressable regions (each of which is commonly referred to as a pixel) and groups of adjacent pixels (or individual pixels) from the detector for each sample are addressed, to enable good resolution to be obtained in the XY sense as between the light from one sample and another.

The charge coupled device may be cooled, for example cryogenically so as to reduce background noise signals associated therewith.

According to a further feature of the invention, the detectors comprise an array of photomultipliers, one photomultiplier for each of the channels (optical paths).

Thus if there are 96 channels, 96 photomultipliers will be required.

Preferably miniature photomultipliers are employed, and where sufficiently small photomultipliers are unavailable, optical fibres or bundles forming cables may be employed to convey the light from each of the apertures in the mask such as is shown in FIG. 4 or 5 of the accompanying drawings, to the 96 windows of 96 photomultipliers which together occupy an area considerably greater than that of the mask.

Alternatively a larger detector lens is employed so that the 96 channels are spread over a larger area.

As previously mentioned, the CCD array may of course be cryogenically or otherwise cooled for the sample purpose, the use of photomultipliers obviates the need for cryogenic cooling.

According to another feature of the invention, the photomultipliers are replaced by an image intensifier or an intensified CCD.

The use of a more sensitive detector such as the use of photomultiplier tubes, an image intensifier or an intensifier CCD, enables time resolved fluorescence of luminescence application to be detected.

In particular the use of a more sensitive detector enables time resolved assay analysis to be performed which involves photo-exciting a fluorophor with a pulsed source of radiation for example a pulsed laser, during which time the detector is gated off so as not to be responsive to any of the excitation radiation and the fluorophor in the assay can be investigated by gating on the detector after a suitable time delay, typically of the order of picoseconds or microseconds, and thereafter reading out the charge pattern in the detector.

Time resolved applications such as described require detectors which can be gated on and off and photomultiplier tubes, image intensifiers and intensified CCD arrangements can be gated in this way electronically so as to enable the delays and short integration periods to be generated as required by time resolved fluorescence or luminescence applications.

In this connection, it is to be understood that the present invention is not limited to fluorescence applications but includes luminescence applications.

Thus the invention is not limited to the nature of the detector or to the technique in which the different regions of the detector are addressed to enable light emanating from one sample to be distinguished from light emanating from another, nor is the invention limited to any of the circuits or computing techniques which may be employed for processing electrical signals obtained by addressing the different regions of the detector array.

Since the spacing between, and the actual size of, the sample sites in a micro-sample array, are very small, and can be of the order of microns, micro lenses, optionally in combination with a fibre optic transfer plate may be employed in the objective lenses adjacent the micro-samples.

In essence the micro-sample objective lenses are equivalent to microscope objectives in that they are short focal length lenses designed to form an image of a tiny object (in this case light being emitted from a small region in a micro-sample). However as distinct from a conventional microscope objective, the optical characteristic of the sample objectives is such as to produce a parallel beam of light therefrom so that in this sense the objective can be said to have one infinite conjugate.

By utilising high quality components and projecting the excitation radiation to the samples via the objective lenses, the excitation radiation can be focused to precisely the regions of interest in the samples, to reduce excitation of surrounding sample material.

Where a filter is located ahead of the detector, apertured masks may be placed on either side of the filter to collimate the parallel beam to further reduce background and crosstalk.

The invention also lies in apparatus adapted to perform the above methods and comprising means for supporting a micro-sample array on a substrate in close proximity but parallel to an array of micro lenses arranged so as to correspond on a one to one basis with the positions and spacing of at least some of the micro-samples on the substrate, each of the micro lenses being positioned relative to a region of its related micro-sample by a distance equal to the focal length of the lens so that light emitted from that region of the micro-sample will emerge from the lens as a parallel beam parallel to the axis of the lens, and the parallel beams of light are focused by means of a single focusing lens through a pinhole aperture onto a detector lens so as to produce an image of the micro-sample light emissions in the plane of an array of individually addressable photoelectric detectors, such as regions of an addressable CCD array, and circuit means is provided to which signals read out from the array are supplied in the form of a sequence of digital values or otherwise, each corresponding to the light incident on a region of the detector for a given period of time from one of the micro-samples, and computing and analysing circuit means is provided, responsive to the electrical signals, together with memory means for storing data indicative of the light found to be emitted from each of the micro-samples, for storing those values together with address information, whereby each stored value can be identified with the micro-sample on the substrate from which the light giving that value has been emitted by reference to the position of the region in the detector array and by correlating the position of the sample in the sample array.

The apparatus may further include a beam splitter, such as a dichroic mirror, interposed in the optical path between the micro lenses and the focusing lens to enable on the one hand light to pass from the lenses to the focusing lens, and on the other hand to enable excitation radiation, typically light of a particular wavelength, to be reflected as a parallel beam towards the micro lenses, thereby utilising the optical focusing characteristics of the micro lenses to focus the parallel light into spots of light which register with the micro-samples so that the latter are individually radiated by excitation light which is predominantly incident on that region of each micro-sample which is to be inspected for fluorescence after the excitation radiation has been removed, and filter means may be provided in the optical path between the beam splitter and the detector array to generally attenuate any excitation wavelength radiation travelling towards the detector and generally prevent such radiation from reaching the detector.

The apparatus preferably includes a pinhole aperture at the focal point of the focusing lens so as to improve the on-axis resolution of the optical system and assist in attenuating unwanted fluorescence such as from background material and other components of an assay ahead of or behind the region of interest in a micro-sample measured along the optical axis of the objective, from reaching the detectors.

The apparatus typically includes a laser source, as the source of excitation radiation a beam expander for enlarging the cross-section of the laser beam and presenting a generally uniform parallel beam of excitation radiation for entry into the imaging system via the beam splitter or dichroic mirror.

Shutter means may be provided to inhibit the passage of the laser light, except when required for excitation purposes, and further shutter means may be provided synchronised with that associated with the laser source to prevent light of any wavelength reaching the detector whilst excitation light is projected into the system.

The invention also comprises a method of analysing fluorescence emitted by radiation excited samples in an array of samples comprising the steps of focusing light emitted from each said sample at infinity so as to form a parallel beam, in parallel with the light from all of the other sample sites making up the array, subsequently focusing all the parallel light paths through a single point and locating at the point a small pinhole aperture to restrict unwanted light from fluorescing material upstream and downstream of the sites of interest in the samples, and re-establishing a parallel array of light beams by the use of a further lens so as to present to an addressable detector array a plurality of parallel light paths corresponding to the light paths from the samples, and individually addressing different regions of the detector array onto which the parallel light paths impinge, to determine the light incident thereon, and storing data relating to the quantity of incident light on each said region of the detector array together with address information to enable the data to be reconciled with the position of the sample in the array on the substrate to which that data relates.

The method typically further comprises the step of introducing periodically into the optical system excitation wavelength illumination and projecting same through the optical imaging devices associated with the array of samples to project the excitation illumination onto a specific region in each said sample, thereafter extinguishing the excitation wavelength light and enabling fluorescence caused by the excitation to pass through the same optical devices to emerge as parallel rays of light for transfer to a detector, for analysis as above mentioned.

The objectives may be arranged above or below a sample array.

The method and apparatus described herein may be used to perform immediate fluorescence analysis (as so far described) or time resolved fluorescence analysis in which a shutter is provided to inhibit the transfer of light to the detector, excitation radiation is supplied for a short interval of time and then shut off (either by pulsing the source out using further shutter or both), after a selected interval of time the shutter preventing transfer of light to the detector is opened and after an appropriate integration interval (which can be very short or longer as described) the residual charge pattern on the charge coupled detector array is interrogated to generate a signal relating to the charge pattern (and therefore indicative of light incident thereon) for processing and storage as aforesaid.

The invention will now be described, by way of example, with reference to the accompanying drawings, in which.

Figure 2:
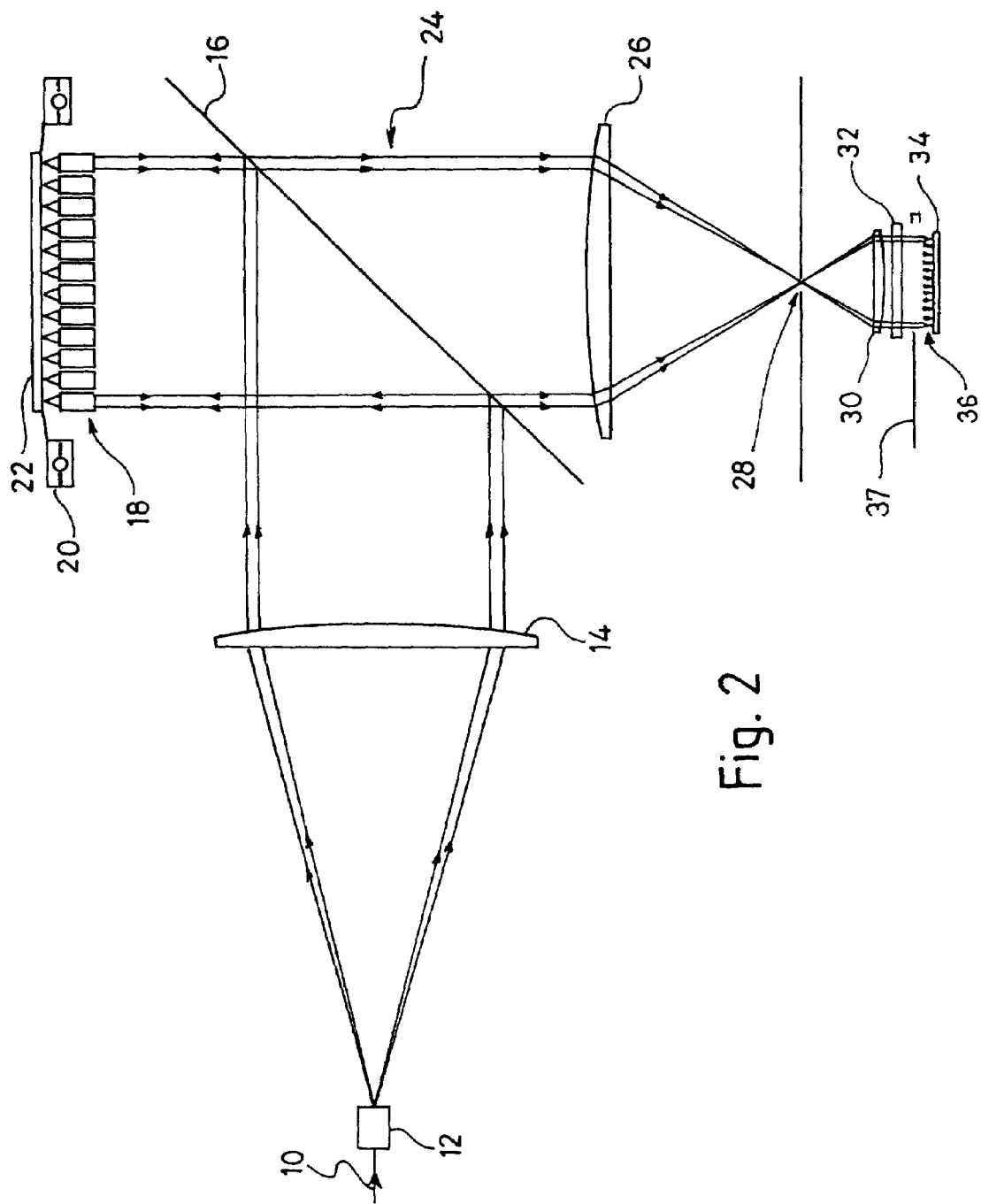
FIG. 2 is a schematic diagram of a confocal imager for measurement of micro-sample assays such as may be contained in an 8×12, 96 well microtitre plate.

FIG. 2 onwards illustrate a unitary, optical scanner which can measure a large number, say 96, of channels simultaneously. The system shown is essentially 96 confocal scanners in parallel, but having a single optic axis, and particularly a single spatial filter in the form of a pinhole aperture. It has all the advantages of scanning confocal microscopy, such as high spatial resolution and good depth discrimination, to interrogate selectively the array of 96 samples, whilst tending to reject fluorescence background from the substrate and surrounds of each of the 96 sites.

One multi channel confocal scanner arrangement is shown in FIG. 2. The example assumes 96 channels.

A laser with sufficient power to illuminate 96 sites simultaneously, comprises a 1 W argon ion laser 10, followed by a beam expander (lenses 12, 14) of suitable diameter and a beam splitter 16. This can deliver at least 10 mW of excitation light (eg of 485 nm for fluorescein) to each of 96 suitable microscope-objective lenses 18 arranged with parallel optic axes in an 8×12 array under an XY stage 20 supporting a multiple micro site assay 22 such as a 96 well microtitre plate.

Alternatively, one could use a conventional, eg filament or arc, source with lenses and with spectral filters to achieve the broad parallel beam required wavelength.

Each lens 18 creates a spot of illumination of—microns in diameter in the region of its micro-site. A suitable lens would be a microscope objective of 10× with NA 0.4, with focal length about 8 mm, and aperture diameter 5 mm.

A normal microscope objective is designed to produce an image of a tiny object being examined at an intermediate focus. This intermediate focus is in turn viewed through an eyepiece. In this invention however, when using a conventional microscope objective, it is preferable for this intermediate focus to be removed to infinity, eg by using a negative (concave) lens (not shown) beyond the microscope objective. In this way, incoming parallel excitation light will produce the required focal spot of excitation light, and a source of fluorescent emission light at the focal spot will likewise produce a beam of parallel light directed towards the focusing lens (see FIG. 2). Another way of putting this is to say that a conventional microscope objective is modified to give optimum spatial resolution with one infinite conjugate.

The emitted fluorescent light returns parallel to the axis of each lens 18, so that the 96 samples result in a wide parallel beam 24 which then passes through the beam splitter into a focusing lens 26, which focuses the light through a single pinhole aperture 28 (spatial filter). This simultaneously allows through all 96 signals but tends to reject the background fluorescent light in any of the channels. This rejection is achieved by the depth discrimination capability of confocal microscopy, since this background fluorescence arises from substrate which is in front of or behind each sample spot and so is out of focus at the pinhole. Also the spatial resolution (say about 10 microns) is sufficiently good to select out background florescence coming from material surrounding laterally each fluorescence sample.

The pinhole diameter may be adjusted to optimise the depth and lateral acceptance. This could be used to adjust the amount of signal measured and the proportion of background that is accepted.

Finally, the light diverging from the pinhole is received by the detector lens of FIG. 2, whose focal plane is at the pinhole. This lens produces a parallel beam which can pass through one or more spectral filters 32, as required.

Figure 4:
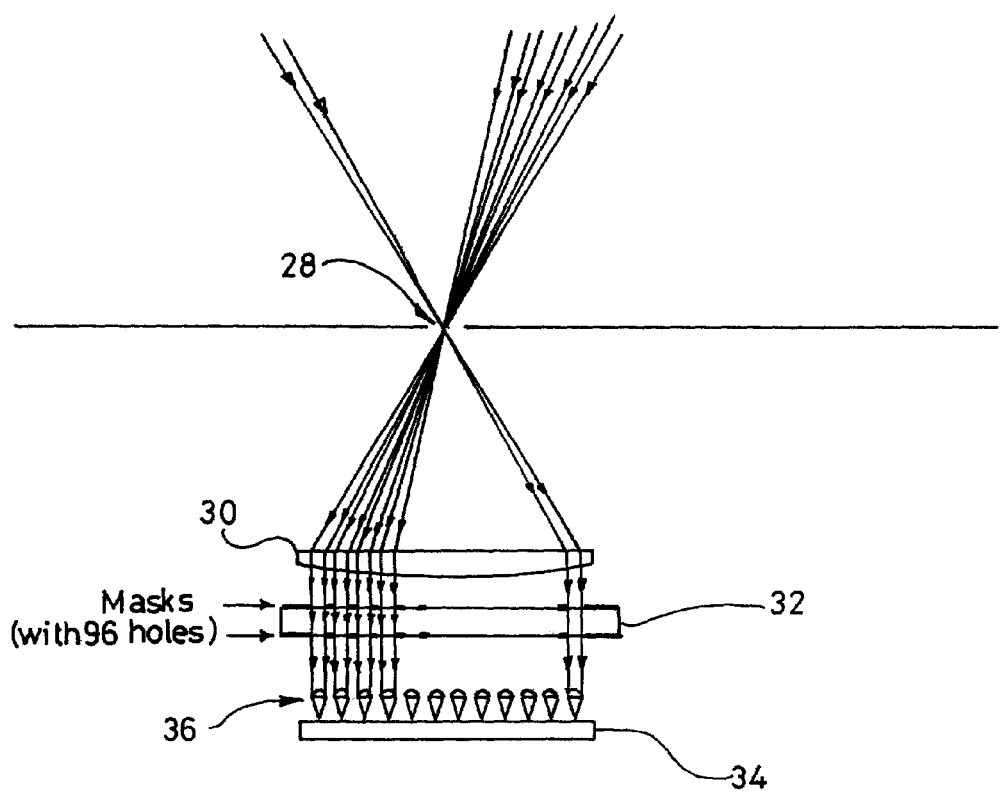
FIG. 4 is a ray diagram indicating in detail the optical arrangement of the pinhole aperture which improves the on-axis resolution of the system.

At this stage the light from each of the 96 samples will form an array of 8×12 bright regions, with separation from each other determined by the separation of the 96 microscope objectives and the focal lengths of the focusing lens and the detector lens. Each bright region will be of diameter approximately equal to that of the microscope objective, but broadened by any residual lens defects and edge scattering at the pinhole, and then reduced by the ratio of the focal length of the detector lens to the focal length of the focusing lens. A detail of the final part of the system, namely the detector optical arrangement, is shown in FIG. 4 which illustrates the 96 parallel beams of light passing through the filter. A mask may be placed on either side of the filter, a shown, to collimate each of the beams as a means of further reducing background (due to scattering and optical defects), and cross-talk.

This array of 8×12 bright regions is detected by a suitable detector array 34, for example an interline CCD with say, 10 Hz frame rate, and of sufficiently small pixel size to give the required spatial resolution. With 10 Hz frame rate one can obtain a succession of images of almost 0.1 second duration, after allowing for dead-time in the detector. Alternatively, an image intensifier or an image intensifier coupled to a CCD, or a series of array of photodiodes, or PMT's, may be used as the detection means. Cooled versions of these detectors may be used, to reduce noise.

To produce an image of the 96 bright regions one could optionally insert an array of 96 micro lenses 36 as shown in FIGS. 2 and 4, position so as to image each region down onto a spot of small size (the order of a millimeter) at the surface of the detector. This will give better definition of each spot on the detector, allow a lower spatial resolution detector to be used, and concentrate the signal over a small area of the detector, hence reducing the effect of background noise in the detector.

Figure 5:
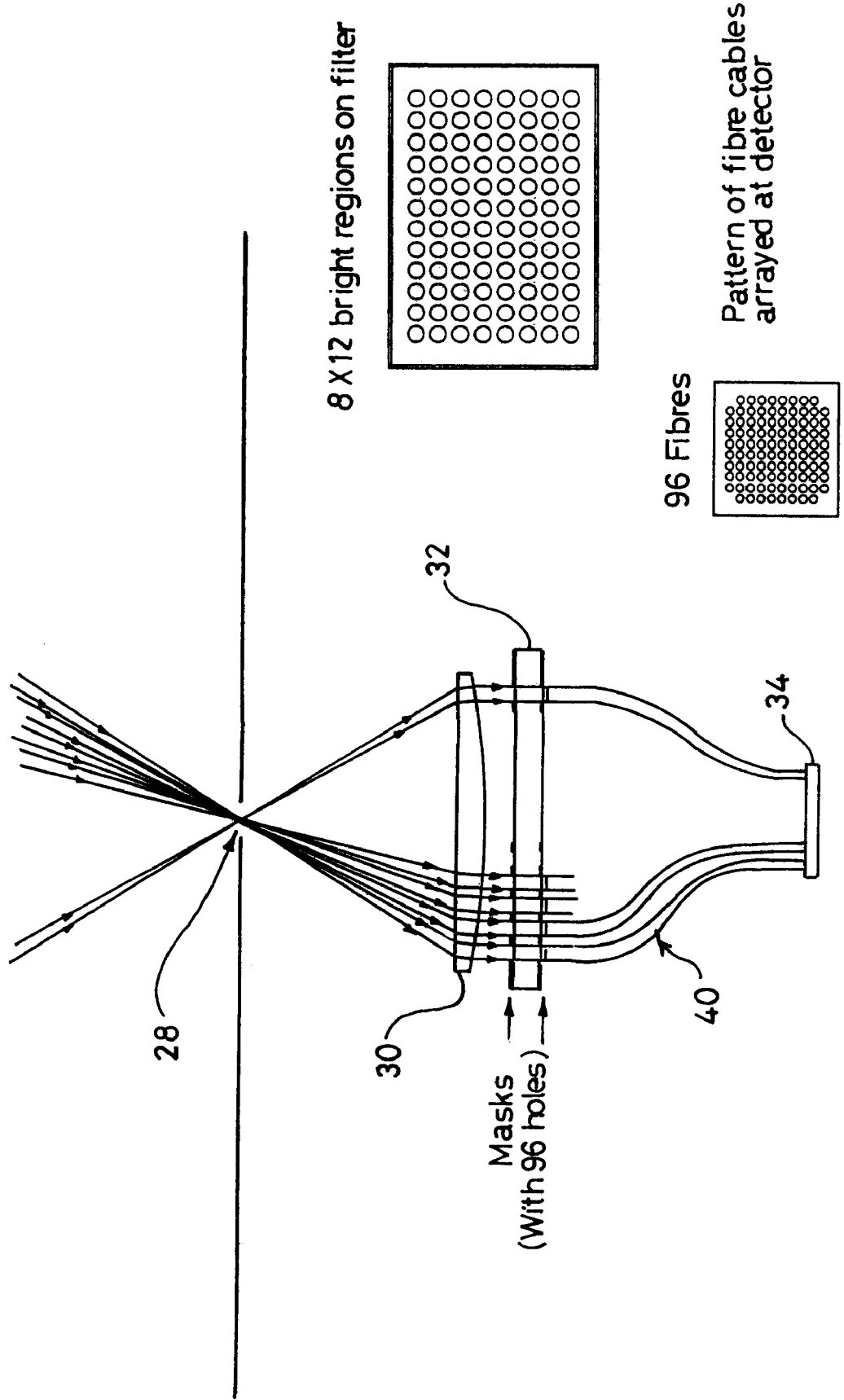
FIG. 5 is a further schematic and ray diagram illustrating how an 8×12 array of light spots can be re-arranged into a pattern having a generally square outline which is more applicable to a typical CCD camera target.

FIG. 5 shows an alternative detector optical arrangement to that shown in FIG. 4, in which an array of fibre optic cables 40 is located immediately after the spectral filter 32, to gather the light from each of the 96 parallel beams emanating from the filter. The far ends of the fibres may be mapped into any arrangement to match the aspect ratio and/or shape and/or area of the detector.

This design is less complex and costly than a "ganged" system of 8 or more independent confocal scanners. It could be extended to more than 96-channels and could also be scaled in size, to examine smaller arrays of tiny sites on an area much smaller than a microtitre plate, for example this could be a high density plate, such as one containing 3456 samples, or a gridded array on a membrane or gel. This could be achieved using smaller components as appropriate, eg an array of micro lenses instead of microscope objectives. To achieve a good result it will obviously be necessary to use high quality lenses throughout, to have the optic axes of the lenses in the scanning array accurately parallel, and to have minimum light scatter from edges etc. This is particularly important for the design of the pinhole aperture, to avoid scatter which could lead to cross-talk between channels.

Another advantage of this invention is that all sites are measured simultaneously, which for a given total measurement time for the whole array means a longer dwell time on a given site and hence more signal and better measurement accuracy.

Note that in FIG. 2 the illumination system, i.e. laser plus beam expander, and the detection system, i.e. focusing lens pinhole, optics and detector, could be interchanged with respect to the beam splitter. The properties of the beam splitter, namely the respective wavelength range of reflected light and transmitted light, would be chosen accordingly. Examples of such a wavelength selecting device include a dichroic mirror or band pass filter. Likewise optical reflectors or mirrors may be used in conjunction with this overall arrangement, to fold, contact or otherwise rearrange optical paths, without affecting the system performance.

Figure 3:
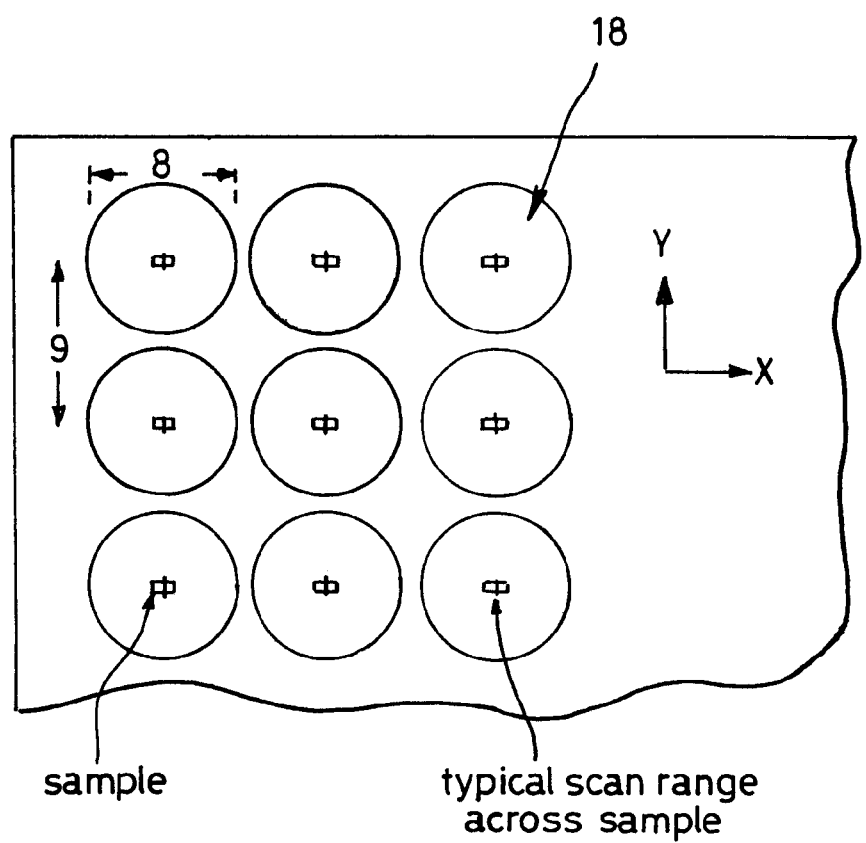
FIG. 3 is a plan view to an enlarged scale of the sample viewing lenses in relation to the samples and typical scan range across each sample.

In FIG. 3 part of a 96-site array is shown positioned relative to the corresponding microscope objective lenses 18. In this example each site comprises a microcapillary aligned in the X-direction, having a width of say, 100 um, in the Y-direction. The depth of the capillary (in the Z-direction) would be typically 50–100 microns. Because of the tolerance in the Y-position of each capillary mentioned above, it would be necessary to move the XY stage in a number of steps in the Y-direction, say 10 steps of 20 um size. At each step a reading, say of 0.1 second direction, is taken. About one-half of the readings will be taken when the scanning spot is within the capillary, and so give useful signal data. The balance of readings would be predominantly of background while the scanning spot moves outside the capillary, and these could be useful as they would give more information about and monitor background in case a correction has to be made for background in the signal.

Figure 1A:
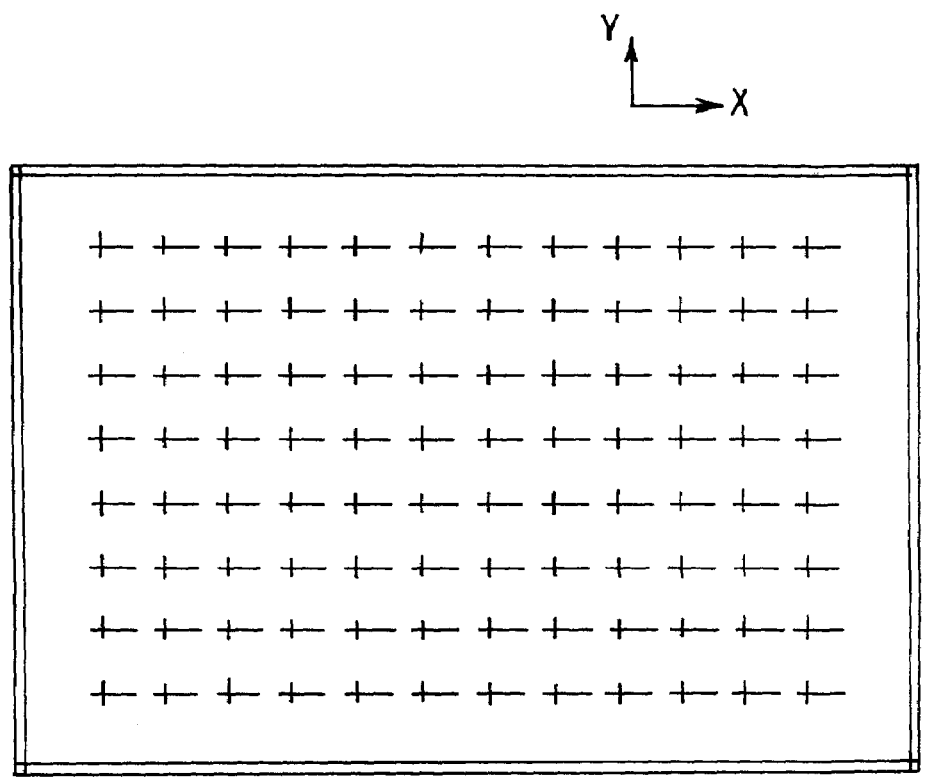
FIGS. 1A, 1B and 1C illustrate arrangements of sample arrays as previously mentioned.
Figure 1B:
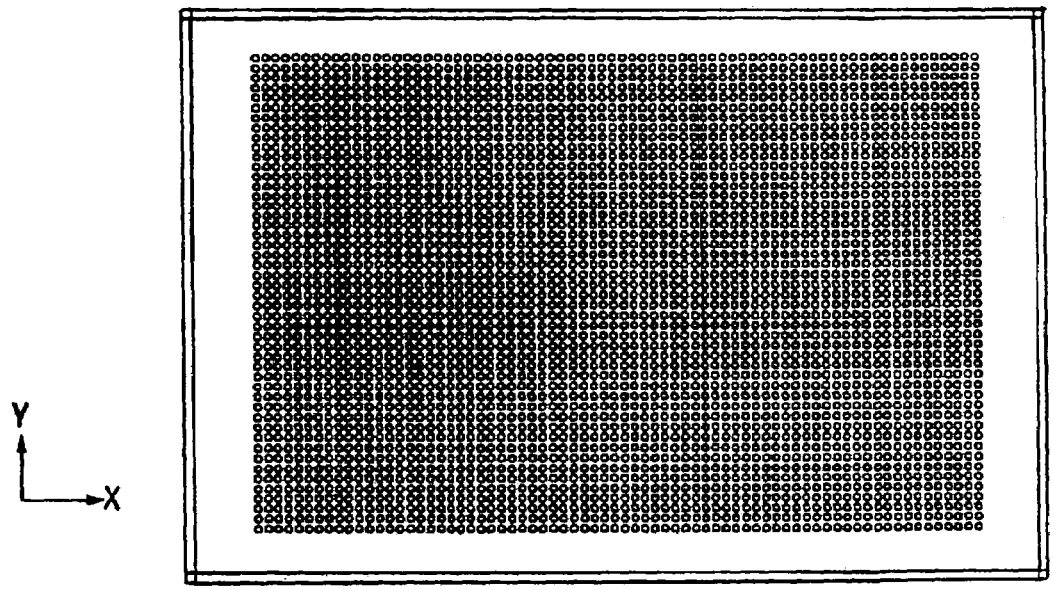
Figure 1C:
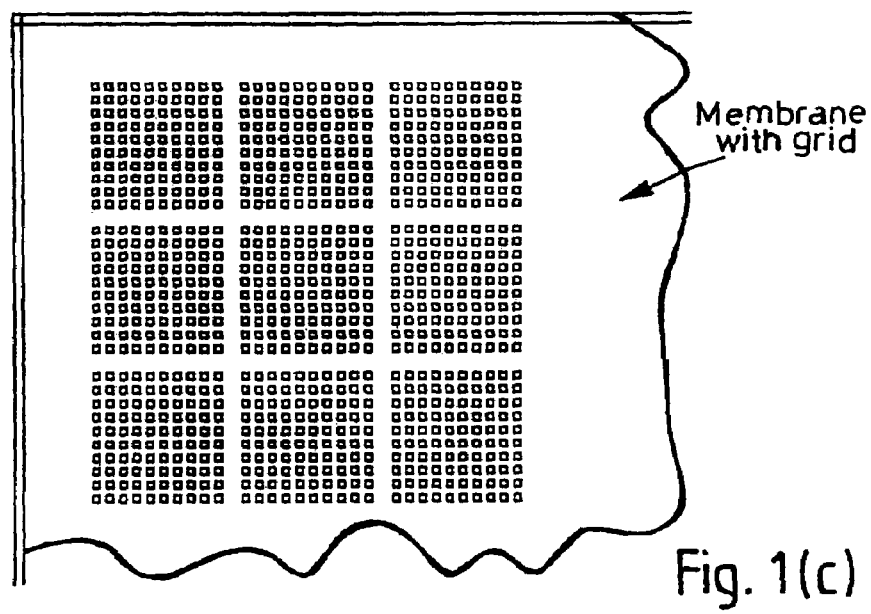

It should be noted that if all the samples are large enough, or sufficiently well defined in location, such as in the Y-direction in our example in FIG. 1(*a*), then scanning might not be necessary. The axes or spots of the multi-channel confocal scanner can be located appropriately on the multiple samples, and measurements made of all samples simultaneously. High density formats can be read by a series of steps across the matrix, as previously described.

In this example 10 readings of the sample are acquired on a continuous basis per second, for each of the 96-sites simultaneously. This rate can be increased as necessary using a faster read-out detector.

This ability to continuously monitor all the sample sites simultaneously has the following advantages in comparison with existing systems which sample periodically, or only sample a small number of the sites at any time.

Firstly the method allows a longer dwell time per site per reading, and hence allows more signal to be detected and hence improves sensitively and accuracy.

In the case, for example, of samples flowing past the detector, such as in micro-capillary electrophoresis where separate peaks pass the detector, the continuous monitoring capability allows better definition of the sample peaks and also allows the flow rate to be monitored and measured more accurately.

Likewise where the level of light emission is changing with time, such kinetic features can be monitored more accurately.

The continuous monitoring capability also allows any quench effect of the light signal, i.e. the interference with or the reduction of the light emission from the sample, to be measured.

In separation processes such as electrophoresis, the molecules or moities in the sample are caused to move in a particular direction (e.g. the X-direction in our FIG. 1(*a*)), and this results in a series of signal peaks being registered or measured by a detector channel as the peaks pass along the fluid matrix. The speed of motion can be chosen within limits. One could take a series of, say 50, sets of readings, each set taking 1 second, so that the plate would take 50 seconds for complete measurement. Assuming a given peak passes the reading spot in 5–10 seconds, this means that one will obtain 5–10 sets of readings of the given peak, each set giving about 5 useful readings of 0.1 seconds each. This ought to be sufficient to give an accurate estimate measurement of the total fluorescence signal from a peak. Several such peaks could be interrogated in the 50 seconds indicated here for the whole measurement process of a plate.

The invention is not limited to the use of any particular fluorophore or wavelength, nor to the specific optical arrangements illustrated herein. Thus the invention is applicable to a wide range of fluorophores and wavelengths and variations can be made in the optical systems described, without departing from the scope of the invention.

The invention claimed is:

1. A method of analysing fluorescence emitted by radiation excited samples in an array of samples, comprising the steps of:
    focusing light emitted from each sample using objective lenses so as to form parallel beams from samples making up the array;
    subsequently focusing the parallel beams through a single point and locating at the single point an aperture to filter out light which is not emanating from one of the focal points of the objective lenses;
    re-establishing a parallel array of light beams by the use of an additional lens so as to present a plurality of parallel beams corresponding to the beams from the samples;

gathering the plurality of parallel beams using optical fibres, which map the beams onto an addressable charge coupled detector array;

individually addressing different regions of the detector array onto which the beams impinge, to determine the light incident thereon; and storing data relating to the quantity of incident light on each said region of the detector array together with address information to enable the data to be reconciled with the position of the sample in the array to which that data relates, in which a shutter is provided to inhibit the transfer of light to the detector array, excitation radiation is supplied for an interval of time and then shut off, after a selected interval of time the shutter inhibiting transfer of light to the detector array is opened, and after an integration interval, the residual charge pattern on the detector array is interrogated to generate a signal relating to the charge pattern for processing and storage as aforesaid.

2. A method according to claim 1, further comprising the steps of: introducing periodically excitation radiation and projecting same onto a specific region in each sample; and thereafter extinguishing the excitation radiation and enabling fluorescence caused by the excitation to pass through the same optical devices to emerge as parallel beams for transfer to the detector array.

3. A method of imaging a plurality of micro-samples simultaneously onto separately addressable detectors so that light emitted from each micro-sample is monitorable by one of the detectors, the method comprising the steps of:

locating a corresponding plurality of objective lenses adjacent to the micro-samples with one objective lens for each micro-sample, the latter being located at or near the focal point of each of the lenses so that light emanating from each micro-sample is collected by its respective objective lens and converted into a beam of parallel or near parallel rays, the objective lenses being arranged so that the beams issuing therefrom are parallel; and focusing the beams by a focusing lens through a single point and collecting the beams beyond that point by detector lens means which serve to reconstitute the parallel beams for presentation to the detectors, in which a pinhole is placed at the focal point of the focusing lens to filter out light which is not emanating from the focal point of each of the objective lenses, wherein a filter is located in front of the detectors, and apertured masks are placed on either side of the filter to collimate the parallel beams to further reduce background and cross-talk.

4. A method according to claim 3, wherein the axes of the objective lenses are angled.

5. A method according to claim 3, wherein the focusing lens is a multi-component lens employed for directing the beams through the single point.

6. A method according to claim 3, wherein the micro-samples are positioned relative to the objective lenses so that the region of interest is as close as possible to the focal point of the respective objective lens.

7. A method according to claim 3, wherein the micro-samples are located on a planar support with the regions of interest in the same plane, and the objective lenses are located in a common plane parallel to that containing the regions of interest in the micro-samples.

8. A method according to claim 3, including the step of:
adjusting the positions of the micro-samples relative to the lenses; and individually adjusting the positions of at least the objective lenses relative to the micro-samples or vice versa so that the regions of interest in the micro-samples are at the focal points of the respective objective lenses.

9. A method according to claim 3, wherein in order to provide spectral separation based on wavelength, a filter is included in the light path either between the micro-sample objective lenses and the focusing lens means ahead of the pinhole, or between the detector lens and the detector array.

10. A method according to claim 9, wherein the filter is located in a region in which the light paths are parallel or nearly parallel.

11. A method according to claim 3, wherein fluorescence generates the radiation which is to be focused onto a detector, and excitation radiation to produce the fluorescence is applied only to a region of interest within each micro-sample rather than over the whole of the micro-sample.

12. A method according to claim 11, wherein excitation radiation is injected so as to proceed in a parallel sense towards the array of objective lenses, in an opposite sense to the light which emanates from the micro-samples, so as to be focused by the objective lenses onto the region of interest in each micro-sample.

13. A method according to claim 12, wherein the excitation radiation is injected as a parallel beam into the optical path, at right angles thereto, onto a 45° beam splitting device, from which it is directed as a parallel beam towards the objective lenses, and radiation from the micro-samples can pass through the beam splitting device to the focusing lens.

14. A method according to claim 3, wherein excitation radiation is produced using a laser, and a beam expander is employed to expand the cross-section of the laser beam into an area equivalent to the area of the array of objective lenses.

15. A method according to claim 3, having an 8×12 array of objective lenses on the same 8×12 matrix as a standard 96 well plate, wherein a well plate is moved using an XY stage relative to the array of objective lenses so as to present groups of 96 wells to the 96 lens array.

16. A method according to claim 3, wherein the parallel beams of light directed towards the detectors are transferred thereto via optical fibres, in the form of a fibre optic bundle or fibre optic plate.

17. A method according to claim 16, wherein a bundle of fibres is employed, the arrangement of the fibres in the bundle differing between the input and output ends thereof so that the shape of the output end of the bundle conforms to the shape of the detector array in the XY plane.

18. A method according to claim 3, wherein the detectors are in a charge coupled device having separately addressable regions.

19. A method according to claim 18, wherein the charge coupled device is cooled.

20. A method according to claim 3 wherein the detectors comprise an array of photomultipliers, one photomultiplier for each beam.

21. A method according to claim 20, wherein each photomultiplier has a window, and optical fibres are employed to convey the light from each of the apertures in a mask to the windows of the photomultipliers, which together occupy an area greater than that of the mask.

22. A method according to claim 20, wherein the photomultipliers are gated electronically.

23. A method according to claim 3, wherein the detectors are in the form of an image intensifier or an intensified CCD.

24. A method according to claim 23 wherein the image intensifier or intensified CCD is gated electronically.

25. A method according to claim 3, wherein additional lenses for focusing the parallel beams of light directed towards the detectors are employed to improve resolution at the detector surface either alone or in combination with a fibre optic transfer bundle.

26. A method according to claim 3, wherein micro-lenses, optionally in combination with a fibre optic transfer plate, are employed in the objective lenses adjacent the micro-samples.

27. A method according to claim 26, in which the micro-lenses have one infinite conjugate.

28. Apparatus for imaging a plurality of micro-sample light emitting sites simultaneously, comprising:
  means for supporting a micro-sample array on a substrate parallel to an array of objective lenses arranged so as to correspond on a one-to-one basis with the positions and spacing of at least some of the micro-samples, each of the objective lenses having a focal length and being positioned relative to a region of its related micro-sample at a distance equal to the focal length of the lens so that light emitted from that region of the micro-sample will emerge from the lens as a parallel beam parallel to the axis of the lens, and the parallel beams of light are focused by means of a single focusing lens onto a detector lens so as to produce an image of the micro-sample light emissions in a plane of an array of individually addressable photoelectric detectors;
  a pinhole aperture at the focal point of the focusing lens to filter out light which is not emanating from one of the focal points of the objective lenses from reaching the detectors;
  shutter means to inhibit the passage of excitation light from a light source, except when required for excitation purposes; and
  additional shutter means synchronised with that associated with the light source to prevent light reaching the detectors whilst excitation light is projected into the system,
  wherein a filter is located in front of the detectors;
  apertured masks are placed on either side of the filter to collimate the parallel beam to reduce background and cross-talk;
  circuit means are provided to which signals read out from the detector array are supplied, each signal corresponding to the light incident on a region of the detector array for a given period of time from one of the micro-samples; and
  computing and analysing circuit means are provided, responsive to the electrical signals, together with memory means for storing values indicative of the light emitted from each of the micro-samples together with detector array address information, whereby each stored value is identifiable with the respective micro-sample.

29. Apparatus according to claim 28, further including:
  a beam splitter interposed in the optical path between the objective lenses and the focusing lens to enable light to pass from the lenses to the focusing lens, and to enable excitation radiation to be reflected as a parallel beam towards the objective lenses, thereby utilising the optical focusing characteristics of the objective lenses to focus the parallel light into spots of light which register with the micro-samples.

30. Apparatus according to claim 28, including a laser source as the source of excitation radiation, and a beam expander for enlarging the cross-section of the laser beam and presenting a beam of excitation radiation for entry into the imaging system via the beam splitter.

31. A method of imaging an array of micro-samples simultaneously onto separately addressable detectors so that light emitted from each micro-sample is monitorable by one of the detectors, comprising the steps of:
  locating a corresponding plurality of objective lenses adjacent to the micro-sample array, with one objective lens for each micro-sample, the latter being located at or near the focal point of each of the lenses so that light emanating from each micro-sample is collected by its respective objective lens and converted into a beam of parallel or near parallel rays, the objective lenses being arranged so that the beams issuing therefrom are parallel;
  focusing the beams with a focusing lens through a single point;
  collecting the beams beyond that point by detector lens means which serve to reconstitute the parallel beams for presentation to the detectors;
  placing a pinhole at the focal point of the focusing lens to filter out light which is not emanating from the focal point of each of the objective lenses;
  providing an array of 96 micro-lenses positioned so as to image each region down on a spot of small size at the surface of the detectors; and
  providing a beam splitter in the optical path between the objective lenses and the focusing lens to enable light to pass from the lenses to the focusing lens, and to enable excitation radiation to be reflected as a parallel beam towards the objective lenses, thereby utilising the optical focusing characteristics of the objective lenses to focus the parallel light into spots of light which register with the micro-samples.

32. Apparatus for imaging a plurality of micro-samples simultaneously, comprising:
  means for supporting a micro-sample array on a substrate parallel to an array of objective lenses arranged so as to correspond on a one-to-one basis with the positions and spacing of at least some of the micro-samples, each of the objective lenses having a focal length and being positioned relative to a region of its related micro-sample at a distance equal to the focal length of the lens so that light emitted from that region of the micro-sample will emerge from the lens as a parallel beam parallel to the axis of the lens, and the parallel beams of light are focused by means of a single focusing lens onto a detector lens so as to produce an image of the micro-sample light emissions in the plane of an array of individually addressable photoelectric detectors;
  a pinhole at the focal point of the focusing lens to filter out light which is not emanating from one of the focal points of the objective lenses from reaching the detectors;
  shutter means to inhibit the passage of excitation light from a light source except when required for excitation purposes;
  an array of 96 micro-lenses positioned so as to image a region of each micro-sample down on a spot of small size at the surface of the detector;
  a beam splitter interposed in the optical path between the objective lenses and the focusing lens to enable light to pass from the lenses to the focusing lens, and to enable excitation radiation to be reflected as a parallel beam towards the objective lenses, thereby utilising the optical focusing characteristics of the objective lenses to focus the parallel light into spots of light which register with the micro-samples;

additional shutter means synchronised with that associated with the light source to prevent light reaching the detectors whilst excitation light is projected into the system;

circuit means to which signals read out from the detector array are supplied, each signal corresponding to the light incident on a region of the detector array for a given period of time from one of the micro-samples;

computing and analysing circuit means, responsive to the electrical signals; and memory means for storing values indicative of the light emitted from each of the micro-samples together with detector array address information, whereby each stored value is identifiable with the respective micro-sample.

33. Apparatus according to claim 32, further including filter means provided in the optical path between the beam splitter and the detector array to substantially prevent excitation radiation from reaching the detector array.

34. Apparatus according to claim 32, including a laser source as the source of excitation radiation, and a beam expander for enlarging the cross-section of the laser beam and presenting a beam of excitation radiation for entry into the imaging system via the beam splitter.

35. A method of imaging a plurality of micro-samples simultaneously onto separately addressable detectors so that light emitted from each micro-sample is monitorable by one of the detectors, comprising the steps of:

locating a corresponding plurality of objective lenses adjacent to the micro-sample array, with one objective lens for each micro-sample, the latter being located at or near the focal point of each of the lenses so that light emanating from each micro-sample is collected by its respective objective lens and converted into a beam of parallel or near parallel rays, the objective lenses being arranged so that the beams issuing therefrom are parallel;

focusing the beams with a focusing lens through a single point;

placing a pinhole at the focal point of the focusing lens to filter out light which is not emanating from the focal point of each of the objective lenses;

collecting the beams beyond that point by detector lens means which serve to reconstitute the parallel beams; and gathering the parallel beams using optical fibres, which map the beams onto the detectors.

36. Apparatus for imaging a plurality of micro-samples simultaneously, comprising:

an array of objective lenses;

means for supporting a micro-sample array on a substrate parallel to the array of objective lenses, the objective lenses being arranged so as to correspond on a one-to-one basis with the positions and spacing of at least some of the micro-samples, each of the objective lenses having a focal length and being positioned relative to a region of its related micro-sample at a distance equal to the focal length of the lens so that light emitted from that region of the micro-sample will emerge from the lens as a parallel beam parallel to the axis of the lens;

a focusing lens for focusing the parallel beams of light through a single point;

a pinhole aperture at the focal point of the focusing lens to filter out light which is not emanating from one of the focal points of the objective lenses from reaching the detectors;

a detector lens for collecting the beams and reconstituting the parallel beams;

optical fibres for gathering the parallel beams and mapping them onto an array of individually addressable photoelectric detectors;

shutter means to inhibit the passage of excitation from a light, except when required for excitation purposes;

additional shutter means synchronised with that associated with the source to inhibit light of any wavelength reaching the detectors whilst excitation light is projected into the system;

circuit means to which signals read out from the array are supplied, each corresponding to the light incident on a region of the detectors for a given period of time from one of the micro-samples;

computing and analysing circuit means, responsive to the electrical signals; and memory means for storing values indicative of the light emitted from each of the micro-samples together with detector array address information, whereby each stored value can be identified with the respective micro-sample.

37. Apparatus according to claim 36, further including a beam splitter in the optical path between the objective lenses and the focusing lens to enable light to pass from the lenses to the focusing lens, and to enable excitation radiation to be reflected as a parallel beam towards the objective lenses, thereby utilising the optical focusing characteristics of the objective lenses to focus the parallel light into spots of light which register with the micro-samples; and filter means in the optical path between the beam splitter and the detector array to substantially prevent excitation radiation from reaching the detector array.

38. Apparatus according to claim 36, including a laser source as the source of excitation radiation, and a beam expander for enlarging the cross-section of the laser beam and presenting a beam of excitation radiation for entry into the imaging system via the beam splitter.

39. A method of measurement of radiation from a plurality of sample sites, wherein a plurality (N) of single channel confocal optical systems and photoelectric detectors or detecting areas are arranged in parallel to form a plurality of reading heads arranged side-by-side so as simultaneously to read a corresponding plurality of adjacent sample sites, comprising the step of independently adjusting the reading heads so that each is accurately positionable over or under a sample site.

40. A method according to claim 39, wherein the sites are arranged in an array, and the optical systems are arranged in a single line for reading column by column a multi-column array, or in a staggered pattern for simultaneously viewing sites in different columns.

41. A method according to claim 39, using (N) independent confocal systems, each with its optic axis aligned with one sample site.

42. A method according to claim 39, wherein light from a single laser source is split into a plurality of beams, each conveyed by a fibre optic cable to an individual sample site.

43. A method according to claim 39, wherein light emitted from the separate sites is conveyed to individual detectors, or discrete regions of an array detector, via optical fibres.

44. A method according to claim 39, wherein an opto-mechanical device is provided to bring each optical system into alignment with a respective site.

* * * * *